US006899873B2

(12) United States Patent
Ma et al.

(10) Patent No.: US 6,899,873 B2
(45) Date of Patent: May 31, 2005

(54) METHOD OF FORMING MICRO-TUBULAR POLYMERIC MATERIALS

(75) Inventors: Peter X. Ma, Ann Arbor, MI (US); Ruiyan Zhang, York, PA (US)

(73) Assignee: The Regents of The University of Michigan, Ann Arbor, MI (US)

( * ) Notice: Subject to any disclaimer, the term of this patent is extended or adjusted under 35 U.S.C. 154(b) by 137 days.

(21) Appl. No.: 10/057,287

(22) Filed: Jan. 25, 2002

(65) Prior Publication Data

US 2002/0150753 A1 Oct. 17, 2002

Related U.S. Application Data

(60) Provisional application No. 60/266,363, filed on Feb. 2, 2001.

(51) Int. Cl.$^7$ ............................. C12N 5/06; C12N 5/08; C12N 11/08; A61F 2/00
(52) U.S. Cl. ...................... 424/93.7; 424/423; 435/180; 435/395
(58) Field of Search ................................ 435/174, 177, 435/180, 395; 424/423, 93.7

(56) References Cited

U.S. PATENT DOCUMENTS

| | | | | |
|---|---|---|---|---|
| 4,481,353 A | 11/1984 | Nyilas et al. | ................ | 528/303 |
| 6,146,892 A | 11/2000 | Ma et al. | ..................... | 435/399 |
| 6,348,069 B1 * | 2/2002 | Vacanti et al. | ............ | 623/11.11 |

OTHER PUBLICATIONS

Langer, R and Vacanti, J., "Tissue Engineering" *Science* 1993, 260 (5110):920–926.
Hubbell JA, "Biomaterials in Tissue Engineering" *Bio/Technology* 1995, 13:565–576.
Zhang R and Ma PX, "Synthetic nano–fibrillar extracellular matrices with predesigned macroporous architectures"., *J. Biomed Mater Rec* 2000, 52(2):430–438.
Ma PX and Choi J., "Biodegradable polymer scaffolds with well–defined interconnected spherical pore network", *Tissue Engineering*, vol. 7, No. 1, 2001, pp. 23–33.
Lu L, Garcia CA, and Mikos AG, "In vitro degradation of thin poly(DL–lactic–co–glycolic acid) films". *Journal of Biomedical Materials Research* 1999, 46(2):236–244.
Ma PX and Zhang R. "Synthetic nano–scale fibrous extracellular matrix" *Journal of Biomedical Materials Research* 1999, 46(1):60–72.
Kim SS, Utsunomiya H., Koski, JA, Wu BM, Cima MJ, Sohn J., Mukai, J, Griffith LG and Vacanti JP, "Survival and function of hepatocytes on a novel three–dimensional synthetic biodegradable polymer scaffold with an intrinsic network of channels" *Annals of Sugery* 1998, 228 (1):8–13.
Ma PX, Schloo B. Mooney D. and Langer R, "Development of biomedical properties and morphogenesis of in vitro tissue engineered cartilage" *J Biomed Mater Res* 1995, 29 (12):1587–1595.

Zhang R and Ma PX, "Poly(alpha–hydroxy acids)/hydroxyaoatite porous composites for bone tissue engineering: 1. Preparation and morphology." *Journal of Biomedical Materials Research* 1999, 44(4):446–455.
Xiao G, Cui Y, Ducy P, Karsenty G, and Franceschi RT, "Ascorbic acid–dependent activation of the ostcocalein promoter in MC3T3–E1 preosteoblasts requirement for collagen matrix synthesis and the presence of an intact OSE2 sequence". *Mol Endocrinol* 1997, 11(8): 1103–1113.
Ma PX, Zhang R., Xiao G and Franceschi R. "Engineering new bone tissue in vitro on highly porous poly(alpha–hydroxyl acids)/hydroxyapatite composite scaffolds." *Journal of Biomedical Materials Research, in press*.
Kam L., Shain W. Turner JN, and Bizios R, "Correlation of astroglial cell function on micro–patterned surfaces with specific geometric parameters". *Biomaterials* 1999, 20(23–24) 2343–2350.
Thomas CH, Lhoest JB, Castner DG, McFarland CD, and Healy KE, "Surfaces designed to control the projected are and shape of individual cells". *J. Biomech Eng.* 1999, 121(1): 40–48.
Kane RS, Takayama S., Ostuni E., Ingber DE, and Whitesides GM, "Patterning proteins and cells using soft lithography", *Biomaterials* 1999, 20 (23–24): 2363–2376.
Schmidt CE, Shastri VR, Vacanti JJP, and Langer R., "Stimulation of neurite outgrowth using an electrically conducting polymer". *Proceedings of the National Academy of Sciences in the United States of America* 1997, 94 (17):8948–8953.
Hudson TW, Evans GR, and Schmidt CE, "Engineering strategies for peripheral nerve repair". *Clin Plast Surg* 1999, 26(4):617–628, ix.
Yannas IV, "Applications of ECM analogs in surgery." *Journal of Cellular Biochemistry* 1994, 56(2): 188–191.

(Continued)

*Primary Examiner*—David M. Naff
(74) *Attorney, Agent, or Firm*—Dierker and Associates, P.C.

(57) ABSTRACT

The present invention discloses the design and fabrication of highly porous (up to 97%) scaffolds from biodegradable polymers with a novel phase-separation technique to generate controllable parallel array of micro-tubular architecture. The porosity, diameter of the micro-tubes, the tubular morphology and their orientation may be controlled by the polymer concentration, solvent system and temperature gradient. The mechanical properties of these scaffolds are anisotropic. Osteoblastic cells are seeded in these 3-D scaffolds and cultured in vitro. The cell distribution and the neo-tissue organization are guided by the micro-tubular architecture. The method has general applicability to a variety of polymers, therefore the degradation rate, cell-matrix interactions may be controlled by the chemical composition of the polymers and the incorporation of bioactive moieties. These micro-tubular scaffolds may be used to regenerate a variety of tissues with anisotropic architecture and properties.

22 Claims, 10 Drawing Sheets

OTHER PUBLICATIONS

Bamber NI, Li H, Aebischer P. and Xu XM. Fetal spinal cord tissue in mind–guidance channels promotes longitudinal axonal growth after grafting into hemiseeted adult rat spinal cords. *Neural Plast* 1999, 6(4):103–121.

"A Tissue–Engineered Conduit for Peripheral Nerve Repair," Hadlock, T.; Elisseeff, J; Langer, R., Vacanti, J; Cheney, M. *Arch Otolaryngol Head Neck Surg* vol. 124, 1081–1086 (Oct. 1998).

"Magnetically Aligned Collagen Gel Filling a Collagen Nerve Guide Improves Peripheral Nerve Regeneration." Ceballos, D; Navarro, X.; Dubey, N; Wendelschafer–Crabb, G; Kennedy, W.R.; Tranquillo, R., *Transactions of the Society for Biomaterials*. 20:295 (1997).

* cited by examiner

METHOD OF FORMING MICRO-TUBULAR POLYMERIC MATERIALS

CROSS-REFERENCE TO RELATED APPLICATIONS

This application claims the benefit of U.S. Provisional application Ser. No. 60/266,363, filed Feb. 2, 2001.

BACKGROUND OF THE INVENTION

The present invention relates generally to methods for fabricating micro-tubular, oriented porous polymeric materials, and more particularly to such methods using a phase separation technique carried out with a directional temperature gradient.

Tissue engineering aims at creating biological alternatives to harvested tissues and organs for transplantation. See, for example, Langer, R. and J. Vacanti, "Tissue engineering," *Science* 260 (5110): 920–926 (1993). Scaffolding plays a crucial role in the three dimensional neo tissue formation. See, for example, Hubbell, J. A., "Biomaterials in Tissue Engineering," *Bio/Technology* 13: 565–576 (1995); Zhang, R. and P. X. Ma, "Synthetic nano-fibrillar extracellular matrices with predesigned macroporous architectures," *Journal of Biomedical Materials Research* 52(2): 430–438 (2000); and Ma, P. X. and J. Choi, "Biodegradable polymer scaffolds with well-defined interconnected spherical pore network," *Tissue Engineering*, 7(1): 23–33 (2001).

Synthetic biodegradable polymers are attractive candidates for scaffolding fabrication because they do not carry the risk of pathogen transmission and immuno-rejection, and because they degrade and resorb after fulfilling the scaffolding function, therefore eliminating the long-term inflammation and complications associated with foreign body reactions. See, for example, Lu, L., C. A. Garcia and A. G. Mikos, "In vitro degradation of thin poly (D,L-lactic-co-glycolic acid) films," *Journal of Biomedical Materials Research* 46 (2): 236–244 (1999); Ma, P. X. and R. Zhang, "Synthetic nano-scale fibrous extracellular matrix," *Journal of Biomedical Materials Research* 46(1): 60–72 (1999); Kim, S. S., H. Utsunomiya, J. A. Koski, B. M. Wu, M. J. Cima, J. Sohn, K. Mukai, L. G. Griffith and J. P. Vacanti, "Survival and function of hepatocytes on a novel three-dimensional synthetic biodegradable polymer scaffold with an intrinsic network of channels," *Annals of Surgery* 228(1): 8–13 (1998); and Ma, P. X., B. Schloo, D. Mooney and R. Langer, "Development of biomechanical properties and morphogenesis of in vitro tissue engineered cartilage," *Journal of Biomedical Materials Research* 29 (12): 1587–1595 (1995).

Each tissue or organ has its characteristic architectural organization, which is closely related to its physiological function. Many organs and tissues have tubular or fibrous bundle architectures. The technology to fabricate single tubular structure at the macro-size scale (a millimeter or larger) such as vascular grafts is available, although the development of perfect vascular grafts is still challenging.

Thus, it would be desirable to provide methods of fabricating polymers into porous materials with non-random, parallel and/or oriented tubular pores throughout the porous materials. It would further be desirable to provide such a method(s) whereby the diameter of the tubules may be controlled from a few to a few hundred micrometers. It would yet further be desirable to provide novel porous materials having oriented micro-tubular architecture, which architecture may advantageously guide cell seeding, distribution, and new tissue formation in vitro and/or in vivo, following the geometrical cues of the micro-tubular architecture in three dimensions. Yet further, it would be desirable to provide such a method(s) wherein the materials may advantageously be natural or synthetic polymers, and/or degradable or non-degradable polymers, and/or blends, mixtures, or composites of polymers.

SUMMARY OF THE INVENTION

The present invention addresses and solves the above-mentioned drawbacks and meets the desiderata enumerated immediately hereinabove by providing a method for forming micro-tubular, oriented porous polymeric materials. The method comprises the steps of: mixing a polymer with a liquid to form a composition; changing the temperature to cause phase separation of the composition with a directional temperature gradient; and then removing an unnecessary phase, thereby forming the micro-tubular, oriented porous polymeric materials.

The method may optionally include the steps of: seeding cells on the micro-tubular materials to form micro-tubular material/cell constructs; and culturing the material/cell constructs within a predetermined tissue culture medium. The culturing may take place in vitro or in vivo.

BRIEF DESCRIPTION OF THE DRAWINGS

Objects, features and advantages of the present invention will become apparent by reference to the following detailed description and drawings, in which.

DETAILED DESCRIPTION OF THE PREFERRED EMBODIMENTS

Figure 1A:
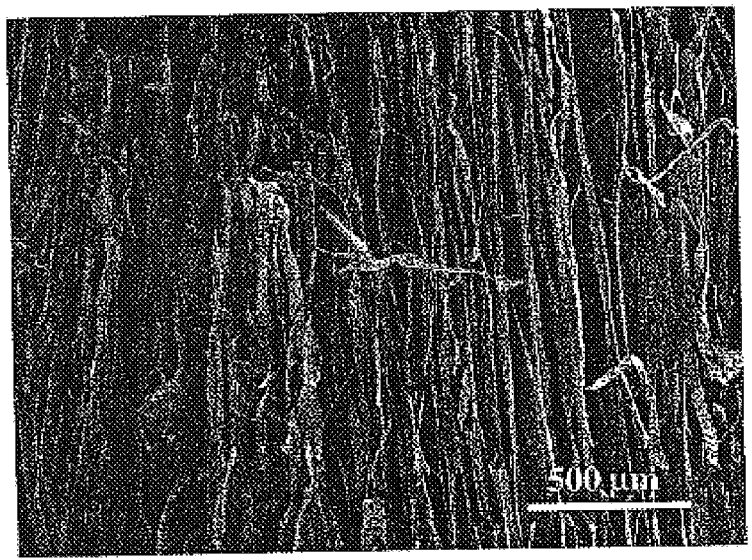
FIG. 1(a) is a SEM micrograph of a longitudinal section of a porous PLLA scaffold prepared in benzene (1.0% (wt/v) PLLA/benzene), the phase separation being carried out with a uni-axial temperature gradient.

The present invention describes novel compositions and methods of fabricating porous materials with tubular pore structures with or without mammalian cells. The method of the present invention provides for the fabrication of a novel biodegradable polymer scaffold of an organized array of open micro-tubules, using a phase separation technique. The present inventive method demonstrates control over the micro-tubule size, porosity, architecture, and mechanical properties with compositional and processing variables. The novel scaffolds of the present invention possess anisotropic mechanical properties. The mechanical properties along the longitudinal direction of the inventive micro-tubules may generally be significantly better than those along a transverse direction to the axis of the tubules.

An important advantage of the present invention is that the novel micro-tubular architecture may guide cell seeding, distribution, and new tissue formation in vitro or in vivo, following the geometrical cues of the micro-tubular architecture in three dimensions.

The diameter of the tubules may be controlled from a few to a few hundred micrometers. The materials may be natural or synthetic polymers. They may be degradable or non-degradable polymers. They may also be blends, mixtures, or composites of polymers.

The novel porous materials of the present invention may be used for a variety of applications, such as scaffolding materials for tissue regeneration, nerve regeneration conduits, medical devices (artificial kidney, dialyzers), matrix materials for reactors or bioreactors, controlled release matrices, wound dressings, separation membranes, filters, porous fillers, catalysis substrates, packaging, and insulating materials. In the present invention, living cells have been cultured in these novel micro tubular materials to form fibrillar and/or tubular new tissues, which may be used as replacement tissues or transplants.

In related work, materials having open random pore architecture have been formed. See, for example, Ma, P. X., R. Zhang, G. Xiao and R. Franceschi, "Engineering new bone tissue in vitro on highly porous poly(alpha-hydroxyl acids)/hydroxyapatite composite scaffolds," *Journal of Biomedical Materials Research*, 54: 284–293 (Nov. 14, 2000); Zhang, R. and P. X. Ma, "Poly(alpha-hydroxy acids)/hydroxyapatite porous composites for bone tissue engineering: 1. Preparation and morphology," *Journal of Biomedical Materials Research* 44 (4): 446–455 (1999). However, the materials described in each of these papers have random architectures—this is in contrast to the controlled, oriented architectures as in the present invention. Although portions of the materials from the papers cited immediately hereinabove may have had what appeared to be an oriented tubular structure, the remainder of the materials were random, ie. oriented in varying directions and/or not tubular at all. In that those materials were not oriented tubular materials therethrough, they were of limited use for certain cell growth and tissue regeneration thereon. As such, those materials required the use of hydroxyapatite (HAP) to promote cell adhesion, growth and differentiation. Although HAP may be used successfully in the present invention if desired, it has been shown that, without HAP, cells grow and follow the geometric cues of the novel oriented tubular architecture.

The present composition consists of the following basic components: polymer or polymers (natural or synthetic, degradable or nondegradable); and liquid (solvent(s) and/or non-solvent(s)). Other components may include: optional materials such as additives (active/bioactive, inert, or temporary) and fillers (ceramics such as hydroxyapatite, tricalciumphosphate and bioglass or metal powders); and/or cells which are primary or cultured cells, cell lines, and/or manipulated cells (genetically or by other means).

Some exemplary polymers of choice include at least one of natural or synthetic hydrophilic polymers, natural or synthetic hydrophobic polymers, natural or synthetic amphophilic polymers, degradable polymers, non-degradable polymers, partially degradable polymers, and mixtures thereof.

Some polymers of choice are degradable polymers selected from at least one of poly(lactide) (PLA), polyglycolic acid (PGA), poly(lactide-co-glycolide) (PLGA), polyanhydrides, poly(ortho esters), and mixtures thereof.

Some exemplary, non-limitative water soluble (hydrophilic) polymers of choice include at least one of polyacrylic acid, polyvinyl alcohol, polyethylene oxide, polyethylene glycol, polymethacrylic acid (PMAA), alginate, collagen, gelatin, hyaluronic acid, and mixtures thereof.

Some exemplary, non-limitative water insoluble (hydrophobic) polymers include at least one of poly(methyl methacrylate) (PMMA), polycarbonate, polypropylene oxide (PPO), polyamides, polyvinylidene fluoride (PVDF), polybutylene, polyacrylonitrile, and mixtures thereof.

Some exemplary, non-limitative degradable polymers (which may or may not be water soluble) include at least one of polyamino acids, engineered artificial proteins, natural proteins, and biopolymers.

Basically, the method of the present invention involves the following steps:

The mixture, solution, dispersion, and/or emulsion is prepared by mixing a polymer or polymers with liquid (solvent, solvents, and/or non-solvent or non solvents) with or without stirring, with heating or without heating.

Some liquids of choice in the present invention include, but are not limited to at least one of acetic acid, acetone, benzene, benzyl alcohol, butyl acetate, n-butyl alcohol, carbon dioxide, carbon tetrachloride, cresol, chlorobenzene, chloroform, cyclohexane, cyclohexanone, dichloroethylene, dimethylformamide (DMF), dioxane, ethyl acetate, ethyl alcohol, ethyl ether, formic acid, heptane, hexane, methanol, methylene chloride, methyl ethyl ketone, octane, propyl alcohol, pyridine, tetrahydrofuran (THF), tetralin, toluene, trifluoroacetic acid, trifluoroethanol, water, xylene, and mixtures thereof. It is believed apparent that the skilled artisan will choose as the liquid a suitable solvent(s) and/or non-solvent(s) depending upon the polymer(s) which is chosen.

The temperature is changed to cause phase separation with a directional temperature gradient (such as unidirectional). In the preferred embodiment, the phase separation temperature ranges between about −196° C. and about 25° C. More particularly, the phase separation temperature may range between about −70° C. and about 0° C.

The unnecessary phase or phases is/are removed (such as solvent(s), non-solvent(s)) through sublimation, liquid exchange, and/or drying (freeze drying).

If desired, cells may be cultured by seeding cells on the micro tubular materials, and culturing the material/cell constructs in an in vivo environment and/or with an appropriate tissue culture medium in an in vitro environment.

Engineering neo-tissues with temporary synthetic extracellular matrices (scaffolds) and mammalian cells is a new approach compared to harvesting tissues for transplantation. Many tissues such as nerve, muscle, tendon, ligament, blood vessel, bone, teeth, etc. have tubular or fibrous bundle architectures and anisotropic properties.

To further illustrate the method and composition of the present invention, the following examples are given. It is to be understood that these examples are provided for illustrative purposes and are not to be construed as limiting the scope of the present invention.

EXAMPLES

Structures of the Porous Materials or Material/Cell Constructs

The inventive compositions have parallel tubular pores with "diameters" (polygon, circular, or other geometric or non-geometric shaped cross-sections) in the size range of a few micrometers to a few hundred micrometers. The tubules can be completely open or with thin partitions in the tubules, or both types of tubules.

When cells are seeded and cultured in the porous micro tubular materials, material/cell constructs or new tissues are formed. The constructs or new tissues are usually organized into tubular or fibrillar structures at least initially.

Scaffold Fabrication

Poly(L-lactic acid) (PLLA) and poly(D,L-lactic acid-co-glycolic acid) (85/15) (PLGA85/15) with inherent viscosity of approximately 1.6 (except where indicated differently) and 1.4 were purchased from Boehringer Ingelheim (Ingelheim, Germany). Poly(D,L-lactic acid-co-glycolic acid) (75/25) (PLGA75/25) with an inherent viscosity of 0.5–0.6 was purchased from Medisorb Technologies International (Cincinnati, Ohio).

The PLLA or PLGAs were dissolved in either benzene or dioxane (both from Aldrich Chemical, Milwaukee, Wis.) to form solutions with desired concentrations. The scaffolds with isotropic pore architecture were fabricated similarly to a procedure previously described for dioxane systems. See, for example, Zhang, R. and P. X. Ma, "Poly(alpha-hydroxy acids)/hydroxyapatite porous composites for bone tissue engineering: 1. Preparation and morphology," *Journal of Biomedical Materials Research* 44 (4): 446–455 (1999).

Briefly, a glass beaker or Teflon vial containing the polymer solution was transferred into a freezer set to a chosen temperature to induce the solid-liquid phase separation. For the oriented micro-tubular scaffolds, the phase separation was carried out with a uni-axial temperature gradient. To achieve this directional temperature gradient, the beaker side was wrapped with a layer of thermal insulating material to reduce the heat transfer through the side wall, and the beaker was set on top of a block of metal in a freezer to increase the heat conduction along the longitudinal direction. The phase-separated polymer/solvent systems were then transferred into a freeze-drying vessel at −5° C. to −10° C. in an ice/salt bath, and was freeze dried under vacuum (pressure lower than 0.5 mm Hg) for two weeks. The dried scaffolds were then kept in a desiccator until characterization or usage.

Structure/Property Characterization

The density and porosity were determined using a method similar to that reported earlier. See, for example, Ma, P. X. and R. Zhang, "Synthetic nano-scale fibrous extracellular matrix," *Journal of Biomedical Materials Research* 46(1): 60–72 (1999). A cube (5 mm×5 mm×5 mm) was cut out of a scaffold sample. The volume was measured accurately from the dimensions, and the mass was measured with an analytical balance. Six specimens were measured to calculate an average density $D_f$. The porosity $\epsilon$ was calculated from the measured scaffold density $D_f$ and the polymer skeletal density $D_p$:

$$\varepsilon = \frac{D_p - D_f}{D_p} \quad (1)$$

where the skeletal density of PLLA was determined by $$D_p = \frac{1}{\frac{1-X_c}{D_a} + \frac{X_c}{D_c}} \quad (2)$$

where $X_c$ was the degree of crystallinity determined with DSC as described elsewhere. See, for example, Ma, P. X. and R. Zhang, "Synthetic nano-scale fibrous extracellular matrix," *Journal of Biomedical Materials Research* 46(1): 60–72 (1999). For PLLA, $D_a$=1.248 g/ml (density of amorphous polymer) and $D_c$=1.290 g/ml (density of 100% crystalline polymer). The density of the amorphous copolymers PLGA85/15 and PLGA75/25 were 1.27 g/ml and 1.30 g/ml, respectively.

The scaffold architectures were examined with scanning electron microscopy (SEM) (S-3200N, Hitachi, Japan) at 15 kV. The specimens were coated with gold using a sputter coater (Desk-II, Denton Vacuum Inc., Moorestown, N.J.).

The compressive mechanical properties of the scaffolds were measured with an MTS mechanical tester (Model:Synergie 200, MTS Systems Corporation, Cary, N.C.). Cubic specimens with a side length of 5 mm were compressed with a cross-head speed of 0.5 mm/min. For samples with anisotropic pore architectures, the load was applied in the direction either parallel to the tubular axis or perpendicular to the tubular axis (transverse direction). The compressive modulus was determined from the initial linear region of the stress-strain curve, and the yield strength was determined from the cross point of the two tangents on the stress-strain curve around the yield point. At least six specimens were tested for each sample, and the averages and standard deviations were graphed. A one-tail student's t-test (assuming unequal variances) was performed to determine the statistical significance ($p<0.05$).

Tissue Culture

The thawed MC3T3-E1 osteoblasts (clone #4, generously provided by Dr. R. Franceschi at University of Michigan, see Xiao, G., Y. Cui, P. Ducy, G. Karsenty and R. T. Franceschi, "Ascorbic acid-dependent activation of the osteocalcin promoter in MC3T3-E1 preosteoblasts: requirement for collagen matrix synthesis and the presence of an intact OSE2 sequence," *Mol. Endocrinol.* 11(8): 1103–1113 (1997); and Ma, P. X., R. Zhang, G. Xiao and R. Franceschi, "Engineering new bone tissue in vitro on highly porous poly(alpha-hydroxyl acids)/hydroxyapatite composite scaffolds," *Journal of Biomedical Materials Research*, 54: 284–293 (Nov. 14, 2000)) were cultured in a supplemental ascorbic acid-free α-MEM (Formula #94-5049EL, 10% FBS, 50 unit/mL penicillin and 50 μg/mL streptomycin) in a humidified incubator at 37° C. with a $CO_2$/air ratio of 5/95. The medium was changed every other day. The cells of passages 3 and 4 were seeded on to the PLLA scaffolds. The viability of the cells before seeding was higher than 90% determined with the trypan blue exclusion assay.

The porous PLLA disks (with isotropic or anisotropic architectures) with a diameter of 10 mm and a thickness of 1.5 mm were prepared from a 5% polymer solution (in either benzene or dioxane). These scaffolds were assembled on the bottoms of custom-made 12-well Teflon culture plates with a well diameter of 10 mm. The scaffold-containing culture plates were sterilized with ethylene oxide. The sterilized PLLA scaffolds (assembled in the wells) were soaked in ethanol for 30 minutes, and then exchanged with phosphate buffered saline for three times (30 min. each). The scaffolds were then washed with a "complete medium" (α-MEM, 10% FBS, 50 unit/mL penicillin, 50 μg/mL streptomycin, and additional 50 mg/L of L-ascorbic acid) for two times (2 hours/each). The medium was then decanted, and 2 million cells (suspended in 0.5 ml of the complete medium) were seeded on each scaffold. The cell-scaffold constructs were cultured on an orbital shaker (Model 3520, Lab-Line Instruments, Melrose Park, Ill.) at 75 rpm in the humidified incubator. The medium was changed two times a day (0.5 ml) for two days. After the 48 hour cell seeding, the polymer-osteoblast constructs were removed from the Teflon plates and transferred into 6-well tissue culture plates. The constructs were cultured with the complete medium on the orbital shaker at 75 rpm in the humidified incubator. Four-milliliter medium was used for each construct, and the medium was changed every other day. Osteoblast-PLLA constructs were cultured in vitro for desired time periods, and then fixed in 10% neutral buffered formalin. Paraffin-embedded disk specimens were cut into 5-micrometer thick cross sections, and stained with hematoxylin and eosin, or von Kossa's silver nitrate.

Results

Micro-tubular Architecture

Figure 1B:
FIG. 1(b) is a SEM micrograph of a longitudinal section of a porous PLLA scaffold prepared in benzene (2.5% (wt/v) PLLA/benzene), the phase separation being carried out with a uni-axial temperature gradient.
Figure 1C:
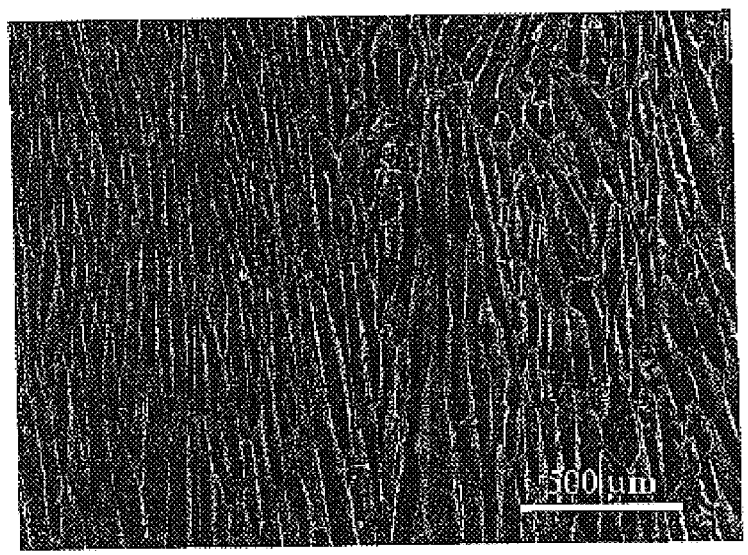
FIG. 1(c) is a SEM micrograph of a longitudinal section of a porous PLLA scaffold prepared in benzene (5.0% (wt/v) PLLA/benzene), the phase separation being carried out with a uni-axial temperature gradient.
Figure 1D:
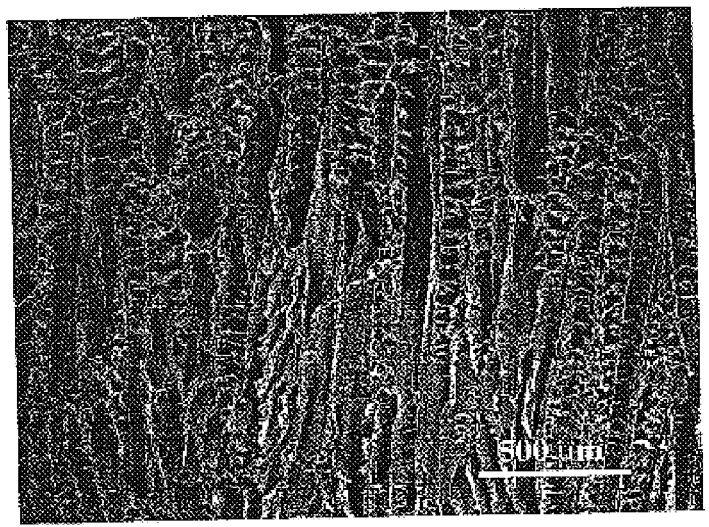
FIG. 1(d) is a SEM micrograph of a longitudinal section of a porous PLLA scaffold prepared in benzene (10.0% (wt/v) PLLA/benzene), the phase separation being carried out with a uni-axial temperature gradient.
Figure 1E:
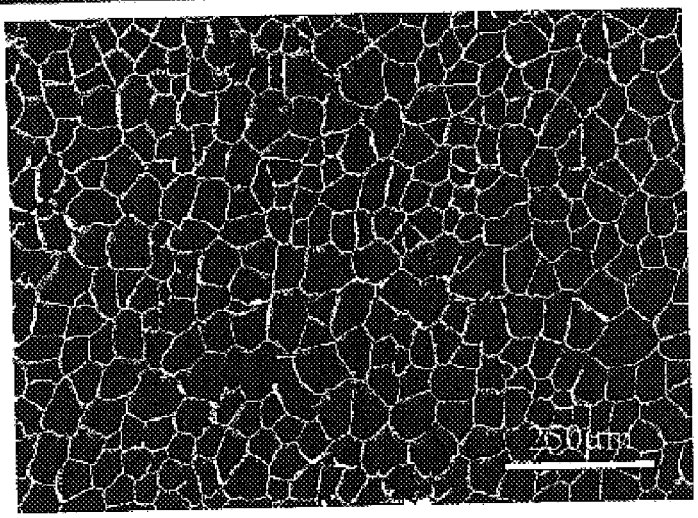
FIG. 1(e) is a SEM micrograph of a cross section perpendicular to the longitudinal direction of a porous PLLA scaffold prepared in benzene (5.0% (wt/v) PLLA/benzene) and having an oriented tubular structure, the phase separation being carried out with a uni-axial temperature gradient.
Figure 1F:
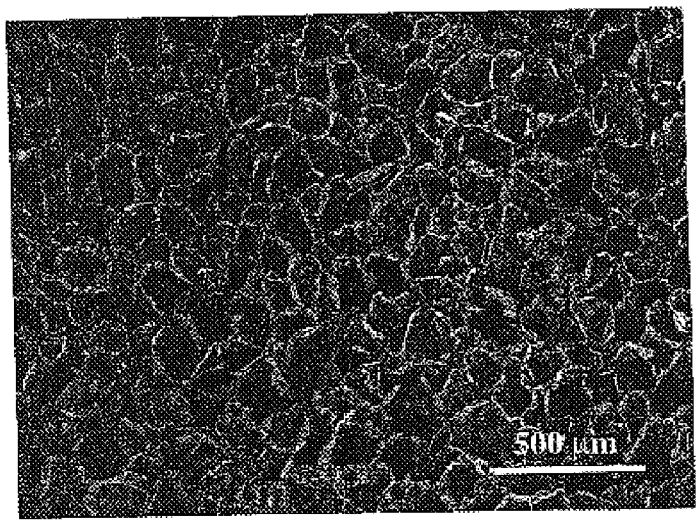
FIG. 1(f) is a SEM micrograph of a cross section in a random direction of a porous PLLA scaffold prepared in benzene (5.0% (wt/v) PLLA/benzene) and having a non-oriented tubular structure, the phase separation being carried out with a non-directional temperature gradient.
Figure 1G:
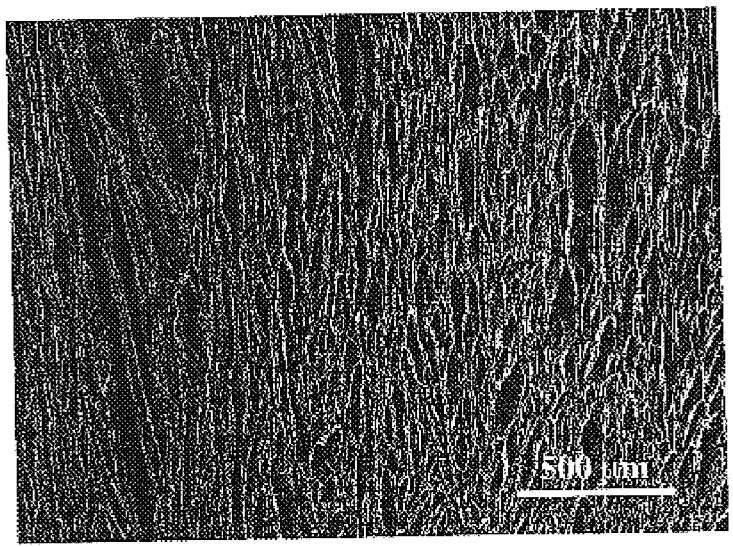
FIG. 1(g) is a SEM micrograph of a longitudinal section of a porous PLGA scaffold prepared in benzene (5.0% (wt/v) PLGA/benzene), the phase separation being carried out with a uni-axial temperature gradient.
Figure 1H:
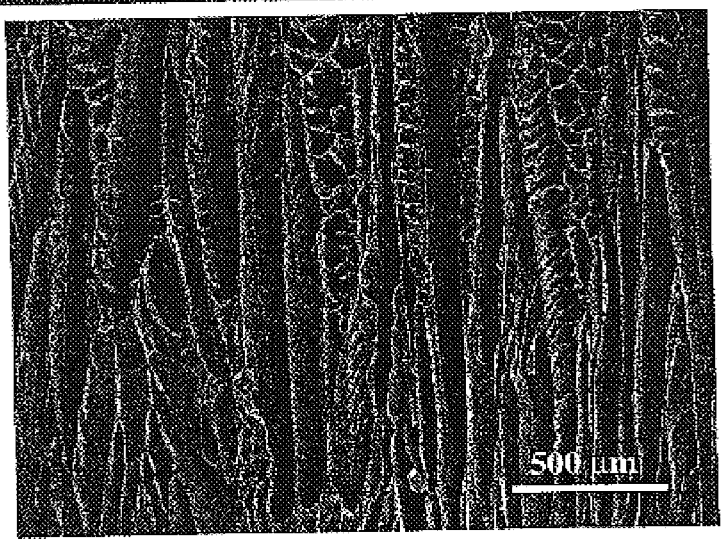
FIG. 1(h) is a SEM micrograph of a longitudinal section of a porous PLLA scaffold prepared in dioxane (5.0% (wt/v) PLLA/dioxane), the phase separation being carried out with a uni-axial temperature gradient.
Figure 1I:
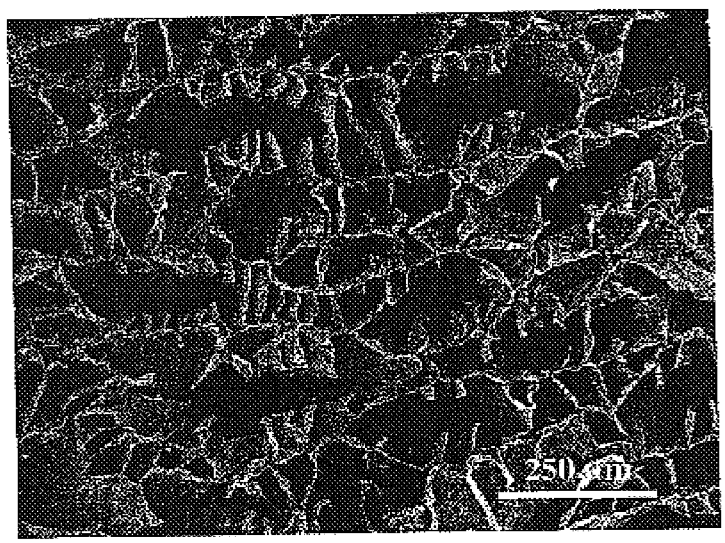
FIG. 1(i) is a SEM micrograph of a cross section perpendicular to the longitudinal direction of a porous PLLA scaffold prepared in dioxane (5.0% (wt/v) PLLA/dioxane) and having an oriented tubular structure, the phase separation being carried out with a uni-axial temperature gradient.

The processing parameters such as temperature gradient, polymer type, solvent type, and the concentration of polymer solution were studied on their effects on the architectural features of the scaffolds. When a temperature gradient was maintained uniaxially during the thermally induced phase-separation process, the characteristic architecture of an array of parallel micro-tubules was achieved (FIGS. 1*a–e* and *g–i*). When the temperature gradient was not uni-axial, the pore architecture was randomly oriented (FIG. 1*f*). At a very low polymer concentration, incomplete tubular architecture (with ribbon and fiber-like features) with minimal mechanical strength was formed (FIG. 1*a*). At suitable polymer concentrations, the architecture of a parallel open micro-tubular array was achieved (FIGS. 1*b, c, e, g*). The cross-sections of the micro-tubules were polygons with 3–7 sides (FIG. 1*e*). At a very high polymer concentration, the resulting scaffolds had an oriented ladder-like (parallel micro-tubes with thin partitions) architecture (FIG. 1*d*). The polymer type (PLLA vs. PLGA—semi-crystalline polymer vs. amorphous polymer) did not have a significant effect on the formation of the micro tubular architecture (FIG. 1*c* vs. *g*). As the concentration of the polymer solution was decreased, the porosity of the formed scaffolds was increased (Table 1). Porosity as high as 97% was achieved with the scaffolds of open micro-tubular architecture. The porosity of the scaffolds was not affected by the directional temperature gradient (tubular architecture), polymer type, or solvent type used (Table 1). The increasing polymer concentration and phase-separation temperature favored ladder-like tubule formation over the open tubular architecture (Table 2). The diameter of the tubules decreased with increasing polymer concentration in the low concentration range, but leveled off above 5% (Table 3). The diameter of the tubules increased with phase-separation temperature (Table 3). The polymer type and molecular weight (viscosity) did not show significant effect on the diameter of the tubules (Table 3).

The solvent type showed a clear effect on the micro architecture of the polymer scaffolds: benzene favored the open tubular structure formation, while dioxane favored the ladder-like structure formation (FIGS. 1*c* and *e* vs. *h* and *i*). This was likely due to the nature of the solid-liquid phase separation, i.e., the crystallization of the solvent to control the architecture formation. The pore geometry was determined by the crystallized solvent, which was subsequently sublimated to form the pores. See, for example Zhang, R. and P. X. Ma, "Poly(alpha-hydroxy acids)/hydroxyapatite porous composites for bone tissue engineering: 1. Preparation and morphology," *Journal of Biomedical Materials Research* 44 (4): 446–455 (1999). A possible reason for benzene and dioxane to result in different pore architectures (open tubular vs. ladder-like) might be due to the difference of the melting points of these two solvents. Because dioxane has a higher melting point (Tm: 11.8° C.) than benzene (Tm: 5.5° C.), the polymer/dioxane solution has a higher degree of super-cooling than that of the polymer/benzene solution at the same phase-separation temperature (−20° C.), which might have resulted in different solvent crystallization kinetics (faster nucleation and slower growth of the dioxane crystals in the polymer/dioxane system) and therefore the different pore architectures of the porous materials. Another possible reason might be that the different polymer-solvent interactions led to different viscosities of the systems, which affected the phase-separation kinetics. The third possible reason might be that the different crystal structures of the two solvents contributed to the differences in the tubular architecture. These factors could have individually or conjointly resulted in the architectural differences in relation to the two different solvents.

Mechanical Properties

Figure 2:
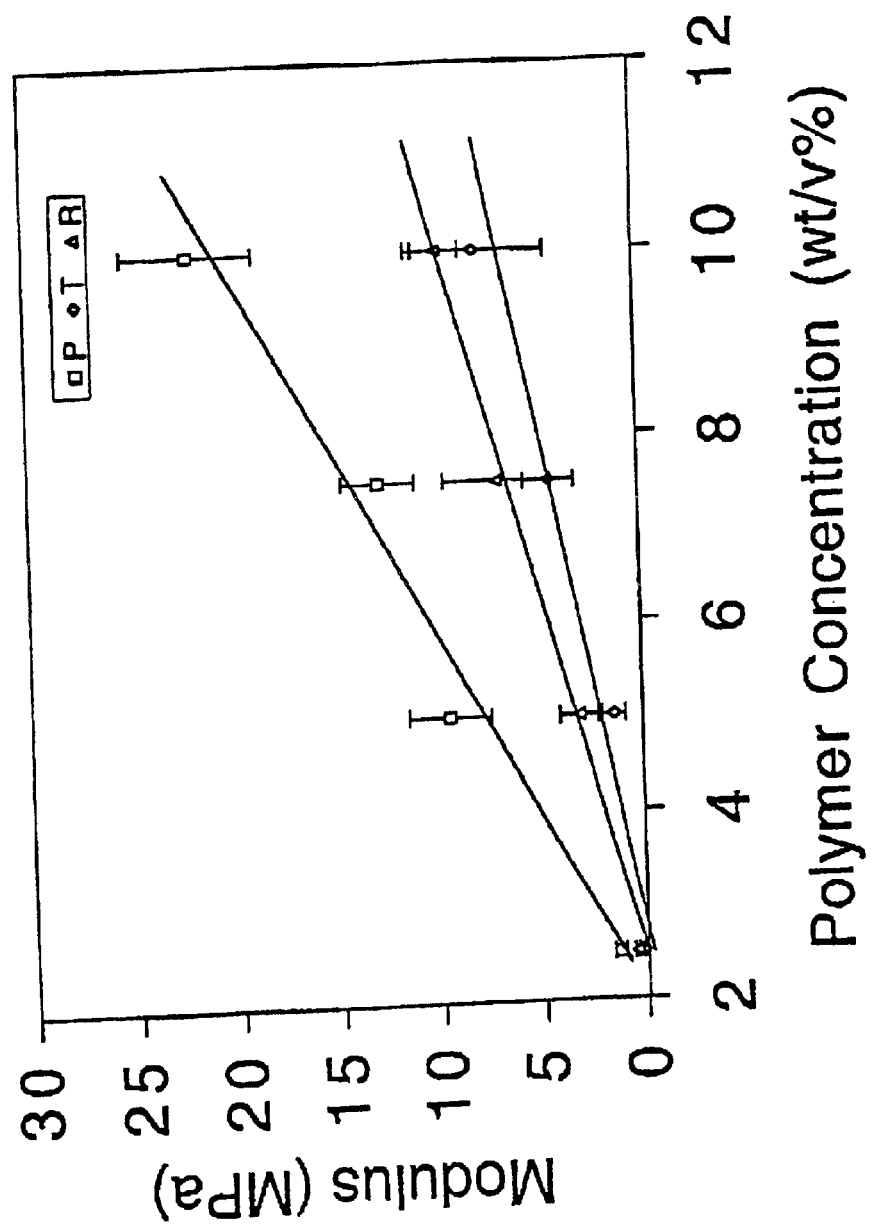
FIG. 2(a) is a graph plotting modulus vs. polymer concentration of scaffolds with tubular or random pore architecture prepared from PLLA/benzene solutions of varying concentrations.
FIG. 2(b) is a bar graph showing modulus of scaffolds prepared from 5.0% (wt/v) PLLA/benzene or PLGA/benzene solution with tubular or random pore architecture.
FIG. 2(c) is a bar graph showing modulus of scaffolds prepared from 5.0% (wt/v) PLLA/benzene or PLLA/dioxane solution with tubular or random pore architecture.
FIG. 2(d) is a graph plotting yield strength vs. polymer concentration of scaffolds with tubular or random pore architecture prepared from PLLA/benzene solutions of varying concentrations.
FIG. 2(e) is a bar graph showing yield strength of scaffolds prepared from 5.0% (wt/v) PLLA/benzene or PLGA/benzene solution with tubular or random pore architecture.
FIG. 2(f) is a bar graph showing yield strength of scaffolds prepared from 5.0% (wt/v) PLLA/benzene or PLLA/dioxane solution with tubular or random pore architecture.
Figure 2:
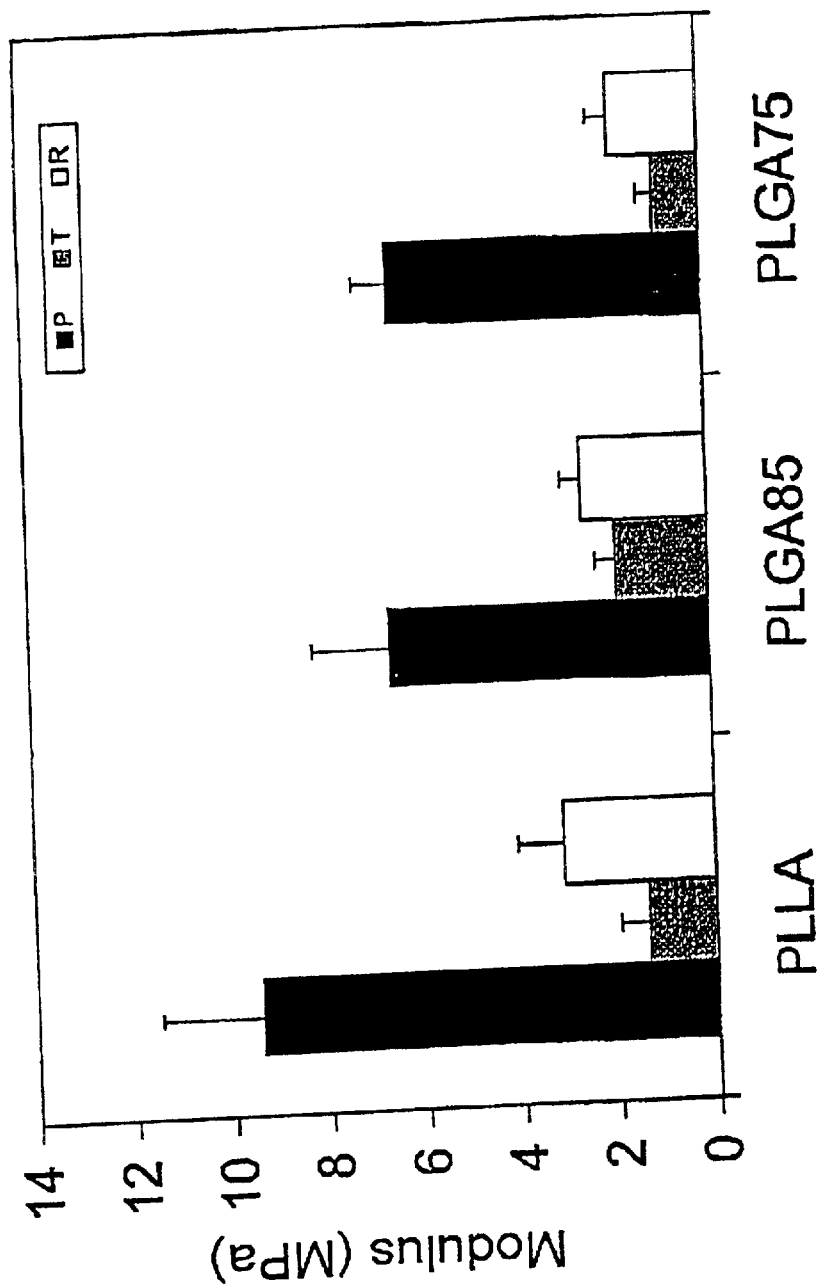
Figure 2:
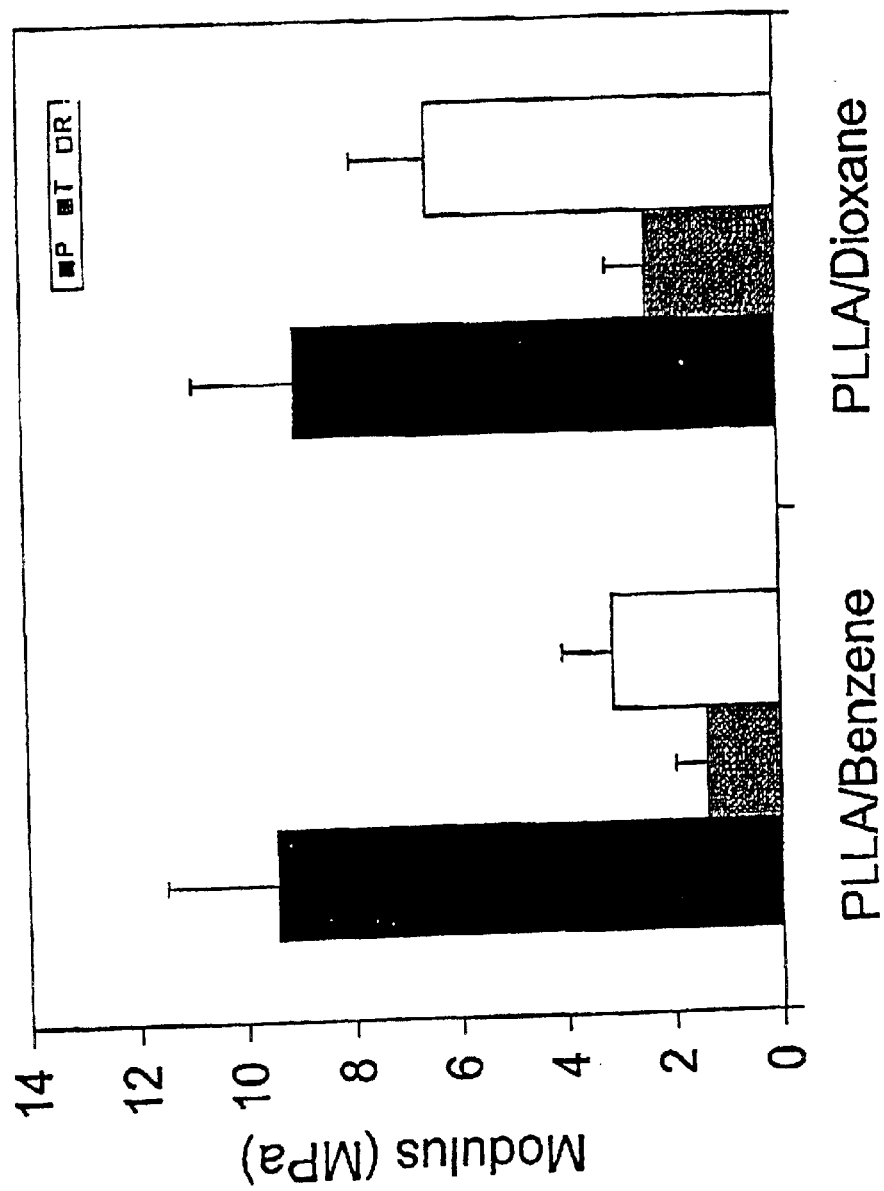
Figure 2:
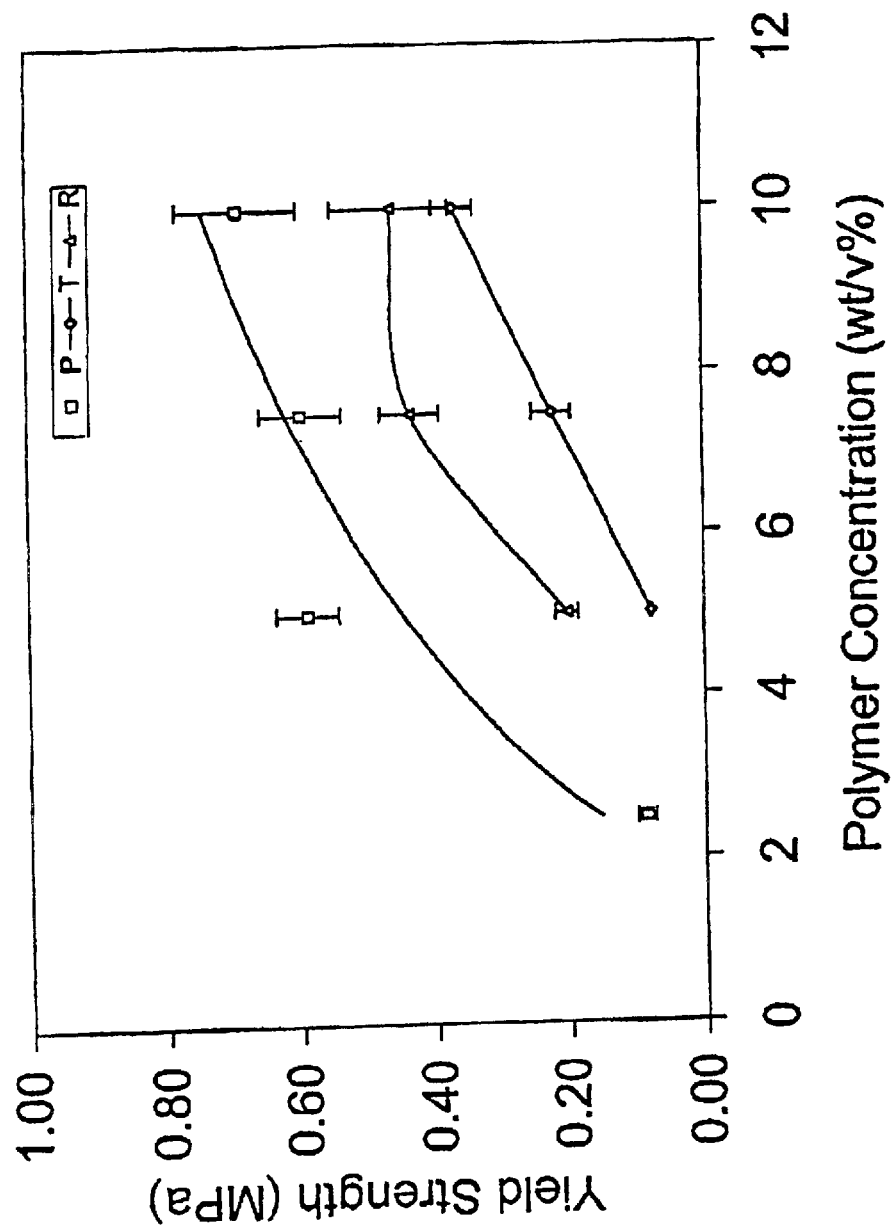
Figure 2:
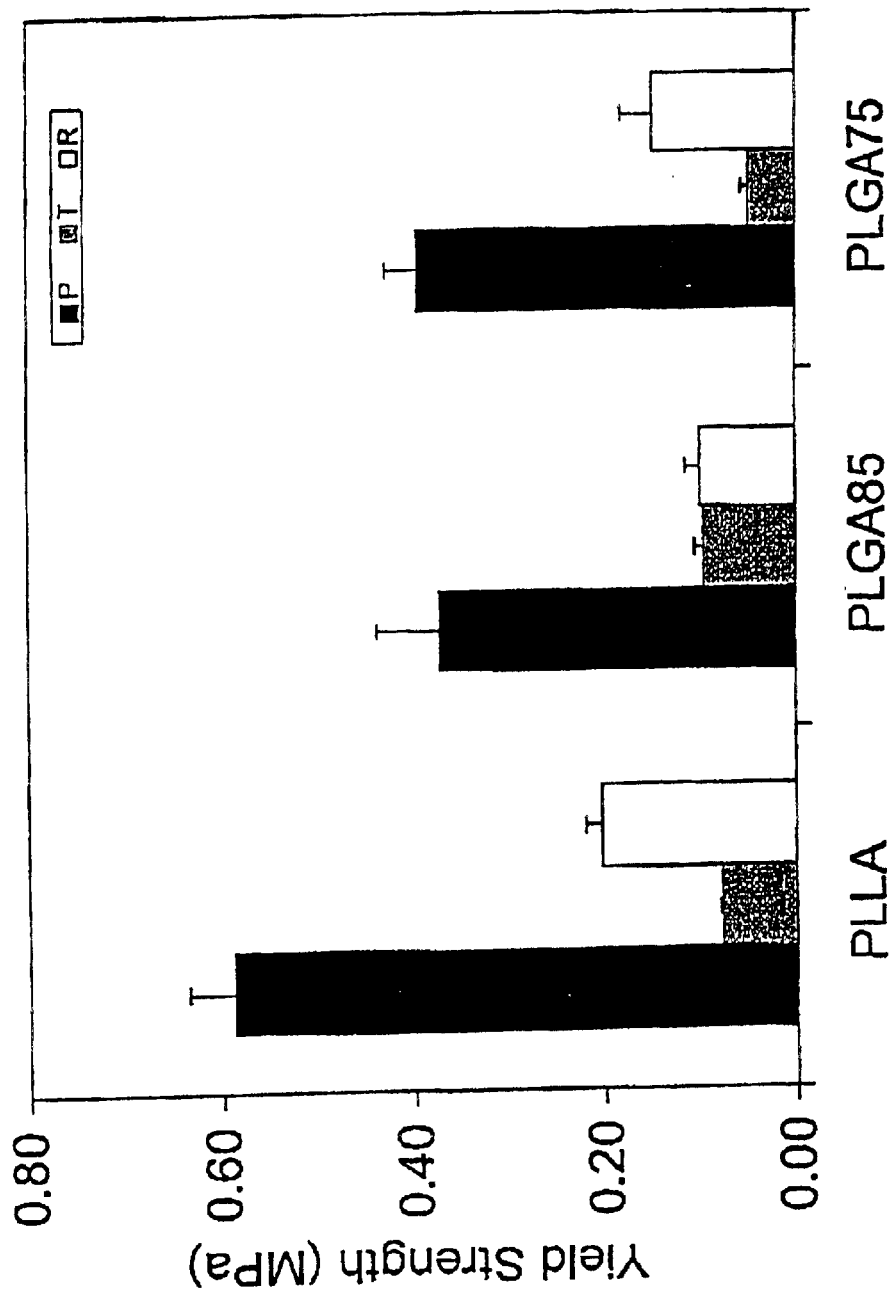
Figure 2:
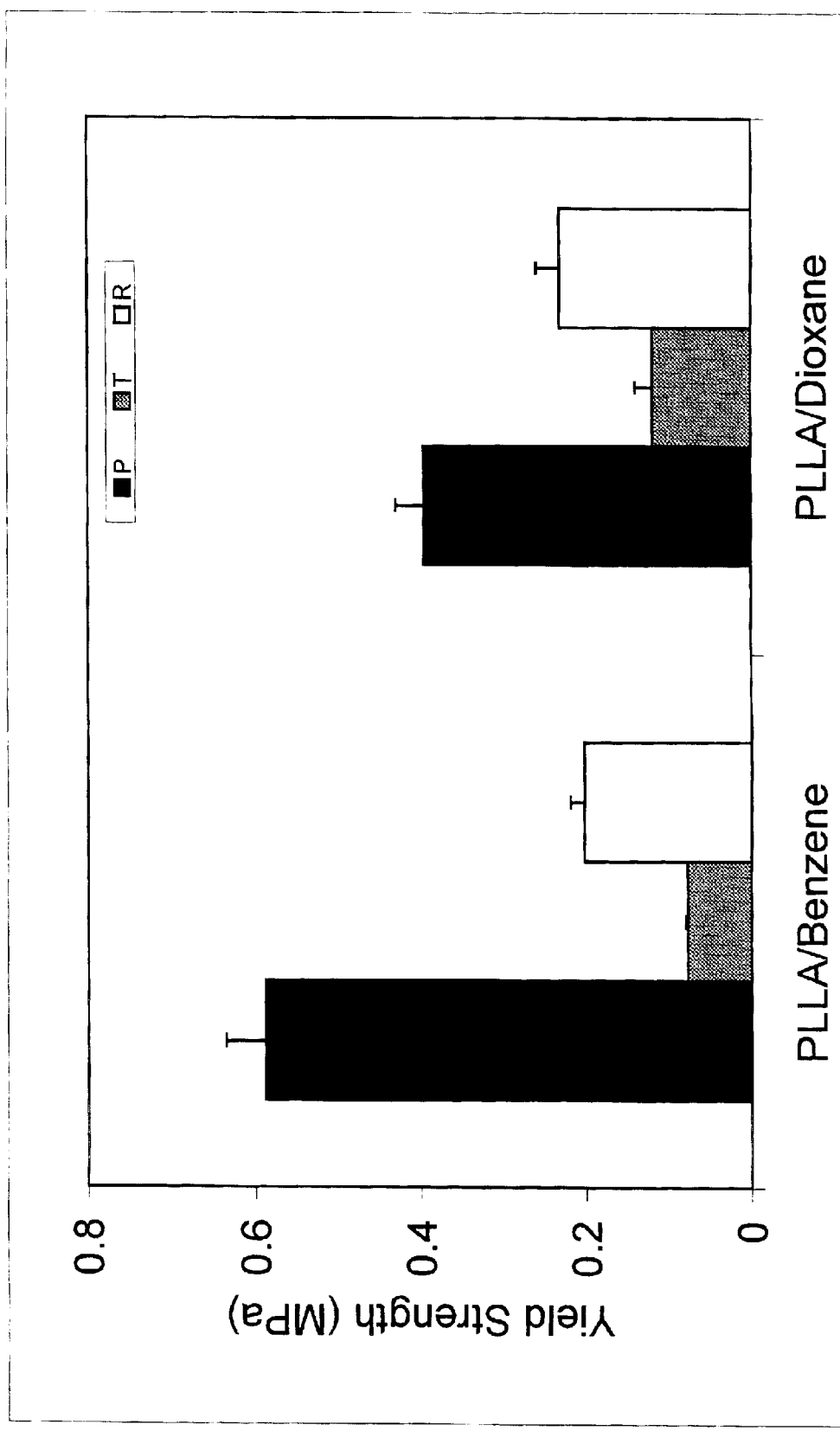

The architectural anisotropy led to anisotropic mechanical properties of the micro-tubular scaffolds. FIG. 2 shows compressive mechanical properties of porous PLLA and PLGA scaffolds prepared with their solutions in benzene or dioxane using a phase-separation technique. In FIGS. 2(a) through 2(f), "P" designates loading direction parallel to the longitudinal direction; "T" designates loading direction along a transverse direction; and "R" designates scaffolds with random pore architecture.

Both the compressive modulus and the yield strength of a scaffold with micro-tubular architecture were significantly greater in the longitudinal direction than in a transverse direction. The scaffolds of isotropic architecture showed isotropic mechanical properties, which fell in between those of the longitudinal and transverse directions of the oriented micro-tubular scaffolds of the same polymer and polymer concentration (FIG. 2). Both the compressive modulus and the compressive yield strength increased with polymer concentration for both the isotropic and anisotropic scaffolds as expected (FIGS. 2a and d). With the same polymer concentration used, the PLLA scaffolds had significantly higher modulus and yield strength than the PLGA copolymer scaffolds (FIGS. 2b and e) in both longitudinal and transverse directions likely due to the crystallinity and higher molecular weight (inherent viscosity) of the PLLA used. The two different oriented architectures (open micro-tubular and ladder-like) of the scaffolds resulted from the two different solvents used (benzene and dioxane) also led to differences in mechanical properties. The modulus of the PLLA scaffolds of parallel open micro-tubular architecture (benzene as the solvent) was slightly higher than that of the scaffolds with a ladder-like architecture (dioxane as the solvent) in the longitudinal direction (FIG. 2c, not statistically significant, p=0.39). The modulus of the scaffold with parallel open micro-tubular architecture was significantly lower (p=0.029) than that of the scaffold with ladder-like architecture in a transverse direction (FIG. 2c). Similarly, the yield strength of the scaffold with the open tubular architecture was significantly higher (p=$6 \times 10^{-5}$) than that of the scaffold with ladder-like architecture in the longitudinal direction while the yield strength of the scaffold with open tubular architecture was significantly lower (p=0.006) than that of the scaffold with ladder-like architecture in a transverse direction (FIG. 2f). The better mechanical properties of the scaffolds with ladder-like structure in the transverse direction were likely due to the contribution of partitions perpendicular to the tubule axis (parallel to the transverse direction). The lower mechanical properties in the longitudinal direction of the scaffold with ladder-like architecture was likely due to the reduced total cross-sectional area of the tubular walls because certain amount of polymer was taken by the partitions.

In vitro Tissue Formation

Figure 3A:
FIG. 3(a) is an optical micrograph of a PLLA scaffold with open micro-tubular architecture prepared from 5.0% (wt/v) PLLA/benzene solution, and incorporating MC3T3-E1 cells therein.
Figure 3B:
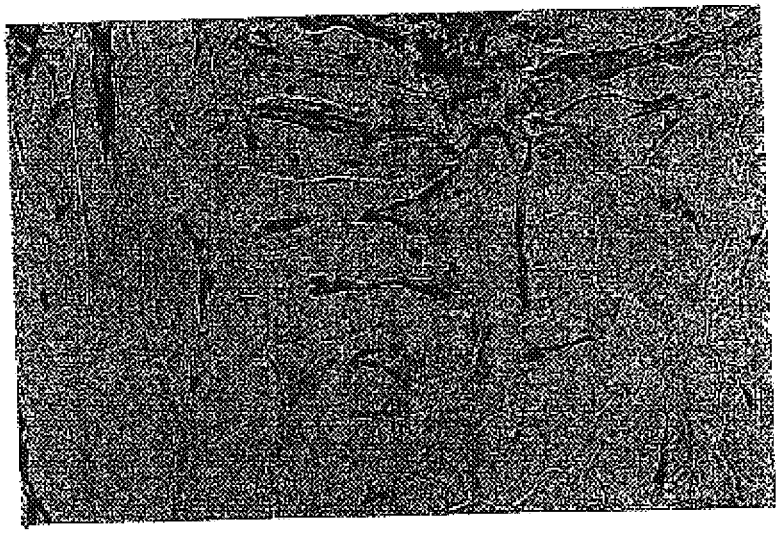
FIG. 3(b) is an optical micrograph of a PLLA scaffold with ladder-like micro-tubular architecture prepared from 5.0% (wt/v) PLLA/dioxane solution, and incorporating MC3T3-E1 cells therein.
Figure 3C:
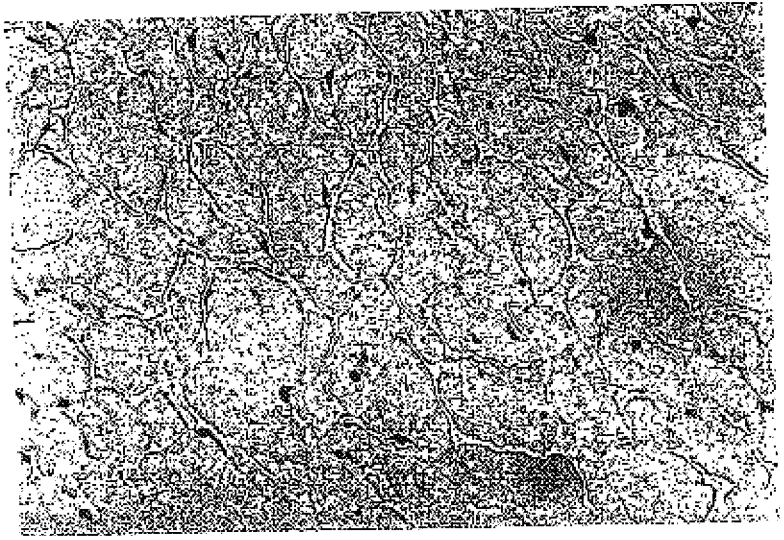
FIG. 3(c) is an optical micrograph of a PLLA scaffold with open random pore architecture prepared from 5.0% (wt/v) PLLA/benzene solution, and incorporating MC3T3-E1 cells therein.

To test if the new tissue formation would follow the clue of the three dimensional architecture of the scaffolds, MC3T3-E1 cells (a well characterized osteoblastic cell line that is known to synthesize bone matrix proteins, see Ma, P. X., R. Zhang, G. Xiao and R. Franceschi, "Engineering new bone tissue in vitro on highly porous poly(alpha-hydroxyl acids)/hydroxyapatite composite scaffolds," *Journal of Biomedical Materials Research*, 54: 284–293 (Nov. 14, 2000)) were seeded on the scaffolds from the same polymer (PLLA) and of the same porosity but with different 3-D architectural features. FIGS. 3(a)–3(c) are SEM micrographs of osteoblasts (MC3T3-E1 clone #4, see method)—scaffold constructs stained with von Kossa's silver nitrate after being cultured in vitro for 4 weeks.

The cell distribution followed the architectural features. After four weeks of in vitro culture, the cells in the open micro-tubular scaffolds were organized along the oriented tubular directions to form oriented neo tissue (FIG. 3a), which was somewhat similar to dentin or long bone in tissue architecture. The cells and the neo tissue in the scaffold of the ladder-like structure were organized along the ladder-like architecture (FIG. 3b). The cells and the neo tissue in a randomly oriented pore scaffold followed the random pore structure (FIG. 3c). Neo tissue formation was more enhanced in the scaffolds of tubular architectures than in that of random pore architecture, which could have resulted from the improved mass transport or/and cell-cell interactions.

Discussion

It is well recognized that scaffold plays a critical role in tissue engineering. There are active research activities in studying the effects of patterning materials surfaces on cell organization in two dimensional models. See, for example, Kam, L., W. Shain, J. N. Turner and R. Bizios, "Correlation of astroglial cell function on micro-patterned surfaces with specific geometric parameters," *Biomaterials* 20 (23–24): 2343–2350 (1999); Thomas, C. H., J. B. Lhoest, D. G. Castner, C. D. McFarland and K. E. Healy, "Surfaces designed to control the projected area and shape of individual cells," *J. Biomech. Eng.* 121(1): 40–48 (1999); and Kane, R. S., S. Takayama, E. Ostuni, D. E. Ingber and G. M. Whitesides, "Patterning proteins and cells using soft lithography," *Biomaterials* 20(23–24): 2363–2376 (1999).

Research in this area has led to significant new understandings in cell-matrix interactions. However, in the body, cells are surrounded by cells and the extracellular matrix in a three dimensional environment. There is little understanding in cell-cell interactions and cell-matrix interactions in these three dimensional systems.

Importantly, the present invention has demonstrated that cells pattern and organize themselves following the architectural clues in the present novel synthetic biodegradable polymer scaffolds in three dimensions. It is believed that this is the first time that cells have been shown to pattern and organize themselves following architectural clues in a synthetic scaffold.

In the body, many tissues such as nerve, muscle, tendon, ligament, vasculature, bone and teeth, have organized fibrillar or tubular architectures. The present invention has successfully created biodegradable polymer scaffolds with the architecture of a parallel array of open micro-tubules, and has demonstrated how to control the architectural parameters such as porosity, diameter of the tubules, and the formation of partitions in the tubular architecture with the processing parameters such as polymer concentration, solvent type, and temperature gradient. As demonstrated with the osteoblastic cells in the present invention, other cell types are likely to follow the architectural clues of the scaffolds to form fibrous bundle or micro-tubular architecture in these novel scaffolds in vitro and in vivo.

The fabrication technology of the present invention is versatile and has the general applicability to other polymers. It has been demonstrated that the solvent type may play a more important role than the polymer type in determining the micro-pore architecture. The biodegradability and the degradation rate may be controlled by designing or selecting the correct chemical structure of the polymer to obtain the desired degradation rate without significantly affecting the scaffolding architecture if the solvent type and the temperature gradient are maintained the same. Similarly, the surface properties of the scaffolds such as hydrophilicity, charge type, charge density, and/or biological functionality may also be manipulated by designing or selecting the correct chemical structure and functionality of the polymers. The internal surfaces of the porous scaffolds may also be modified post scaffold fabrication. The technology may also be used to fabricate scaffolds of polymer blends, mixtures, and composites with the desired micro-tubular architectures. Therefore, the technology can be used to fabricate matrices with both cell delivery and bioactive molecule delivery capabilities. The micro-tubular architecture of the present invention may serve as superior scaffolds for the engineering of a variety of tissues with fibrillar or tubular architectures.

To guide peripheral nerve repair, tubes made of natural and synthetic materials have been used. See, for example, Schmidt, C. E., V. R. Shastri, J. P. Vacanti and R. Langer, "Stimulation of neurite outgrowth using an electrically conducting polymer," *Proceedings of the National Academy of Sciences of the United States of America* 94 (17): 8948–8953 (1997); Hudson, T. W., G. R. Evans and C. E. Schmidt, "Engineering strategies for peripheral nerve repair," *Clin. Plast. Surg.* 26 (4): 617–628, ix (1999); Yannas, I. V., "Applications of ECM analogs in surgery," *Journal of Cellular Biochemistry* 56(2): 188–191 (1994); and Bamber, N. I., H. Li, P. Aebischer and X. M. Xu, "Fetal spinal cord tissue in mini-guidance channels promotes longitudinal axonal growth after grafting into hemisected adult rat spinal cords," *Neural. Plast.* 6 (4): 103–121 (1999). However, a large hollow tube is not as effective as tubes filled with oriented fibrous (see Ceballous, D., X. Navarro, N. Dubey, G. Wendelschafer-Crabb, W. R. Kennedy and R. T. Tranquillo, "Magnetically aligned collagen gel filling a collagen nerve guide improves peripheral nerve regeneration," *Exp. Neurol.* 158 (2): 290–300 (1999)) or tubular (see Hadlock, T., J. Elisseeff, R. Langer, J. Vacanti and M. Cheney, "A tissue-engineered conduit for peripheral nerve repair," *Arch. Otolaryngol Head Neck Surg.* 124(10): 1081–1086 (1998)) materials.

The new fabrication technology developed in the present invention can create the parallel multi-tubule structure in a one-step phase separation process. The polymers may be biodegradable and biocompatible. The porosity and pore size can be controlled. The fabrication technology has the potential to incorporate bioactive factors, and the scaffold can be designed for the growth of nerve supporting cells such as Schwann cells. Therefore, the scaffolds can be tailored into synthetic guidance for nerve repair.

Many tissues with anisotropic structures such as tendon, ligament, muscle, bone, and dentin also have anisotropic mechanical properties. The present invention has demonstrated the anisotropic mechanical properties of these micro-tubular scaffolds, which might match the mechanical properties better to those of the tissues to be replaced or repaired.

With the capability of controlling a variety of chemical and architectural features of the open micro-tubular scaffolds, the new scaffolding technology may advantageously be used to generate tailor-designed scaffolds for the engineering of a variety of oriented tubular or fibrillar tissues. The technology may also be used to fabricate novel porous materials (from degradable or non-degradable polymers) for other biomedical and industrial applications such as wound dressing, controlled release, substrate for biological and chemical reactions, extra-corporal devices (e.g., artificial kidney), filtration membrane, insulating, packaging, and mechanically dampening materials.

TABLES

TABLE 1

Densities and Porosities of the PLLA and PLGA Scaffolds.

| Polymer | Solvent | Concentration (wt/v %) | Phase-separation Temperature (° C.) | Pore Structure | Density (g/cm³) | Porosity (%) |
|---|---|---|---|---|---|---|
| PLLA | Benzene | 2.5 | −20 | tubular | 0.038 | 97.0 |
| PLLA | Benzene | 2.5 | −20 | random | 0.037 | 97.1 |
| PLLA | Benzene | 5.0 | −20 | tubular | 0.078 | 93.8 |
| PLLA | Benzene | 5.0 | −20 | random | 0.074 | 94.1 |
| PLLA | Benzene | 7.5 | −20 | tubular | 0.105 | 91.7 |
| PLLA | Benzene | 7.5 | −20 | random | 0.110 | 91.3 |
| PLLA | Benzene | 10.0 | −20 | tubular | 0.140 | 88.9 |
| PLLA | Benzene | 10.0 | −20 | random | 0.141 | 88.8 |
| PLLA | Dioxane | 5.0 | −20 | tubular | 0.084 | 93.3 |
| PLLA | Dioxane | 5.0 | −20 | random | 0.084 | 93.4 |
| PLGA85/15 | Benzene | 5.0 | −20 | tubular | 0.079 | 93.7 |
| PLGA85/15 | Benzene | 5.0 | −20 | random | 0.074 | 94.1 |
| PLGA75/25 | Benzene | 5.0 | −20 | tubular | 0.086 | 93.5 |
| PLGA75/25 | Benzene | 5.0 | −20 | random | 0.073 | 94.2 |

TABLE 2

Percentage of tubules with ladder-like architecture changes with PLLA/benzene concentration and phase-separation temperature.

| Polymer | Concentration (wt/v %) | Phase-separation Temperature (° C.) | Percentage of Ladder-like Tubules |
|---|---|---|---|
| PLLA | 5.0 | −20 | 13.0 |
| PLLA | 7.5 | −20 | 40.4 |
| PLLA | 10.0 | −20 | 48.5 |
| PLLA | 12.5 | −20 | 54.9 |
| PLLA | 15.0 | −20 | 63.5 |
| PLLA | 5.0 | Liquid N₂ | 0 |
| PLLA | 5.0 | −10 | 30.5 |

TABLE 3

Average diameter of micro-tubules changes with the polymer concentration and phase-separation temperature

| Polymer | Inherent Viscosity (dl/g) | Concentration (wt/v %) | Phase-separation Temperature (° C.) | Average Diameter (μm) |
|---|---|---|---|---|
| PLLA | 1.6 | 2.5 | −20 | 96.3 |
| PLLA | 1.6 | 5.0 | −20 | 61.5 |
| PLLA | 1.6 | 7.5 | −20 | 61.2 |
| PLLA | 1.6 | 10.0 | −20 | 54.9 |
| PLLA | 1.6 | 12.5 | −20 | 54.7 |

TABLE 3-continued

Average diameter of micro-tubules changes with the polymer
concentration and phase-separation temperature

| Polymer | Inherent Viscosity (dl/g) | Concentration (wt/v %) | Phase-separation Temperature (° C.) | Average Diameter (μm) |
|---|---|---|---|---|
| PLLA | 1.6 | 15.0 | −20 | 59.1 |
| PLLA | 1.6 | 5.0 | Liquid N$_2$ | 28.2 |
| PLLA | 1.6 | 5.0 | −10 | 71.5 |
| PLLA | 1.6 | 5.0 | 0 | 113.4 |
| PLGA (85/15) | 1.4 | 5.0 | −20 | 54.1 |
| PLLA* | 1.0* | 5.0 | −20 | 57.9 |

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A method for forming micro-tubular polymeric materials, the method comprising the steps of:
   mixing at least one polymer with a liquid to form a composition at a first temperature;
   causing phase separation of the composition to form a first phase and a second phase by exposing the composition to a uni-axial temperature gradient extending along a predetermined axis from a first region of the composition at a second temperature to a second region of the composition at a third temperature; and then
   removing the first phase, thereby forming the micro-tubular polymeric materials comprising a plurality of micro-tubules having a predetermined architecture with each of the plurality of micro-tubules arranged substantially parallel to each other, substantially uniformly throughout the materials.

2. The method as defined in claim 1 wherein the architecture is adapted to guide at least one of cell seeding, cell distribution, and new tissue formation in vitro or in vivo, via geometrical cues from the micro-tubular architecture in three dimensions.

3. The method as defined in claim 1, further comprising the steps of:
   seeding cells on the micro-tubular materials to form micro-tubular material/cell constructs; and
   culturing the material/cell constructs.

4. The method as defined in claim 3 wherein the architecture is adapted to guide at least one of the cell seeding, cell distribution, and new tissue formation in vitro or in vivo, via geometrical cues from the micro-tubular architecture in three dimensions.

5. The method as defined in claim 3 wherein the culturing takes place in vitro within a predetermined tissue culture medium.

6. The method as defined in claim 3 wherein the culturing takes place in vivo.

7. The method as defined in claim 1 wherein the polymer is chosen from at least one of natural or synthetic hydrophilic polymers, natural or synthetic hydrophobic polymers, natural or synthetic amphophilic polymers, degradable polymers, non-degradable polymers, partially degradable polymers, and mixtures thereof.

8. The method as defined in claim 7 wherein the polymer is selected from at least one of poly(lactide) (PLA), polyglycolic acid (PGA), poly(lactide-co-glycolide) (PLGA), polyanhydrides, poly(ortho esters), and mixtures thereof.

9. The method as defined in claim 7 wherein the polymer is a water soluble (hydrophilic) polymer selected from at least one of polyacryiic acid, polyvinyl alcohol, polyethylene oxide, polyethylene glycol, polymethacrylic acid (PMAA), alginate, collagen, gelatin, hyaluronic acid, and mixtures thereof.

10. The method as defined in claim 7 wherein the polymer is a water insoluble (hydrophobic) polymer selected from at least one of poly(methyl methacrylate) (PMMA), polycarbonate, polypropylene oxide (PPO), polyamides, polyvinylidene fluoride (PVDF), polybutylene, polyacrylonitrile, and mixtures thereof.

11. The method as defined in claim 7 wherein the polymer is a degradable polymer selected from at least one of polyamino acids, engineered artificial proteins, natural proteins, and biopolymers.

12. The method as defined in claim 8 wherein the polymer is at least one of poly(L-lactic acid) (PLLA) and poly(D,L-lactic acid-co-glycolic acid) (PLGA).

13. The method as defined in claim 1 wherein the liquid is at least one of a solvent, a mixture of solvents, a mixture of a solvent and a non-solvent, a mixture of solvents and non-solvents, and mixtures thereof.

14. The method as defined in claim 13 wherein the liquid is at least one of acetic acid, acetone, beezene, benzyl alcohol, butyl acetate, n-butyl alcohol, carbon dioxide, carbon tetrachloride, cresol, chlorobenzene, chloroform, cyclohexane, cyclohexanone, dichloroethylene, dimethylformamide (DMF), dioxane, ethyl acetate, ethyl alcohol, ethyl ether, formic acid, heptane, hexane, methanol, methylene chloride, methyl ethyl ketone, octane, propyl alcohol, pyridine, tetrahydrofuran (THF), tetralin, toluene, trifluoroacetic acid, trifluoroethanol, water, xylene.

15. The method as defined in claim 12 wherein the liquid is a solvent selected from at least one of benzene, dioxane, and mixtures thereof.

16. The method as defined in claim 1 wherein the first phase is removed by at least one of sublimation, liquid exchange, drying, and a combination thereof.

17. The method as defined in claim 1 wherein the phase separation temperature ranges between about −196° C. and about 25° C.

18. The method as defined in claim 15 wherein the phase separation temperature ranges between about −70° C. and about 0° C.

19. The method as defined in claim 1 wherein each of the plurality of micro-tubules has a diameter ranging between about 28.2 micrometers and about 113.4 micrometers.

20. Micro-tubular polymeric materials formed by the method of claim 1.

21. The materials as defined in claim 20, further comprising cells seeded on the micro-tubular materials, thereby forming micro-tubular material/cell constructs.

22. The materials as defined in claim 20 wherein each of the plurality of micro-tubules has a diameter ranging between about 28.2 micrometers and about 113.4 micrometers.

* * * * *